US012751624B2

(12) United States Patent
Matters et al.

(10) Patent No.: US 12,751,624 B2
(45) Date of Patent: Oct. 6, 2026

(54) RECOMMENDER SYSTEM USING COGNITIVE PRE-TESTING TO SELECT OPTIMAL MRI SCANNING TASKS

(71) Applicant: KONINKLIJKE PHILIPS N.V., Eindhoven (NL)

(72) Inventors: Marco Matters, Valkenswaard (NL); Evelijne Machteld Hart de Ruijter-Bekker, Waalre (NL); Maria Estrella Mena Benito, Eindhoven (NL); Raymond Van Ee, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 150 days.

(21) Appl. No.: 18/727,116

(22) PCT Filed: Jan. 4, 2023

(86) PCT No.: PCT/EP2023/050090
§ 371 (c)(1),
(2) Date: Jul. 8, 2024

(87) PCT Pub. No.: WO2023/135040
PCT Pub. Date: Jul. 20, 2023

(65) Prior Publication Data

US 2025/0090023 A1 Mar. 20, 2025

(30) Foreign Application Priority Data

Jan. 12, 2022 (EP) .................................... 22151080

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/16* (2013.01); *A61B 5/7267* (2013.01);
(Continued)

(58) Field of Classification Search
CPC ... G01R 33/4806; G01R 33/543; G16H 30/20
(Continued)

(56) References Cited

U.S. PATENT DOCUMENTS 9,317,580 B2 * 4/2016 Cohen-Solal .......... G16H 70/20
10,068,351 B2 * 9/2018 Lachner .................... G06T 5/92
(Continued)

FOREIGN PATENT DOCUMENTS

EP 3381353 A1 10/2018
WO 2021001238 A1 1/2021

OTHER PUBLICATIONS

Pradyumna Lanka et.al Malini (Machine Learning in NeuroImaging): A Matlab toolbox for aiding clinical diagnostics using resting-state fMRI data; Data in Brief, vol. 29, 2020, 105213, ISSN 2352-3409, https://doi.org/10.1016/j.dib.2020.105213.
(Continued)

*Primary Examiner* — Christopher P Mcandrew

(57) ABSTRACT

In order to improve MRI workflow, a recommender system is provided that comprises an input unit, a processing unit, and an output unit. The input unit is configured to receive data comprising information about a plurality of pre-tests provided to a patient and associated pre-test results. The plurality of pre-tests is performed prior to an MRI scan session. The plurality of pre-tests comprises a cognitive test, a sensorimotor test, or a combination thereof. The processing unit is configured to generate, based on the received data, a cognitive profile of the patient indicative of an individual's pattern of relative strengths and difficulties across several
(Continued)

cognitive domains. The processing unit is further configured to determine, based on the cognitive profile of the patient, a task implementation for the MRI scan session. The processing unit is further configured to provide, via the output unit, a recommendation of the determined task implementation for the MRI scan session.

15 Claims, 3 Drawing Sheets

(51) Int. Cl.
*A61B 5/16* (2006.01)
*G01R 33/48* (2006.01)
*G01R 33/54* (2006.01)

(52) U.S. Cl.
CPC ....... *G01R 33/4806* (2013.01); *G01R 33/543* (2013.01)

(58) Field of Classification Search
USPC .......................................................... 324/309
See application file for complete search history.

(56) References Cited

U.S. PATENT DOCUMENTS

| | | | | |
|---|---|---|---|---|
| 10,943,407 | B1 * | 3/2021 | Morgan | G06T 19/006 |
| 11,043,307 | B2 * | 6/2021 | Smurro | G06Q 10/0633 |
| 2007/0167724 | A1 | 7/2007 | Gadagkar et al. | |
| 2010/0145182 | A1 | 6/2010 | Schmidt et al. | |
| 2014/0010432 | A1 * | 1/2014 | Cohen-Solal | G16H 50/20 382/131 |
| 2014/0180060 | A1 | 6/2014 | Parrish et al. | |
| 2018/0060533 | A1 * | 3/2018 | Reicher | G16H 10/60 |
| 2019/0001133 | A1 * | 1/2019 | Onarheim | A61N 1/36025 |
| 2019/0198158 | A1 * | 6/2019 | Beymer | G16H 30/40 |
| 2021/0186330 | A1 * | 6/2021 | Hall | A61B 5/0042 |
| 2022/0037018 | A1 * | 2/2022 | Goede | G06F 18/251 |

OTHER PUBLICATIONS

International Search Report and Written Opinion from PCT/EP2023/050090 mailed Mar. 17, 2023.

* cited by examiner

RECOMMENDER SYSTEM USING COGNITIVE PRE-TESTING TO SELECT OPTIMAL MRI SCANNING TASKS

CROSS REFERENCE TO RELATED APPLICATIONS

This application is a U.S. national phase application of International Application No. PCT/EP2023/050090 filed on Jan. 4, 2023, which claims the benefit of EP Application Serial No. 22151080.3 filed on Jan. 12, 2022 and is incorporated herein by reference.

FIELD OF THE INVENTION

The present invention relates to a recommender system and a method for determining magnetic resonance imaging (MRI) scanning tasks, to a computer program element, and to a computer-readable medium.

BACKGROUND OF THE INVENTION

MRI techniques, such as functional MRI (fMRI), have given the possibility to investigate non-invasively the cognitive processes in healthy populations and different disorders, such as neurological and psychiatric disorders.

Currently, functional MRI is mostly performed with a task-based approach. In this method, patients are requested to perform cognitive or sensorimotor tasks. At present, most standard tasks are selected based on the clinical symptoms or suspected problem of the patient. However, for a more reliable clinical diagnostics and/or prognostics, MRI data should be examined on the level of individual case. Given individual variations in brain anatomy and organization, analysis on the level of the single person may be important to improve the interpretation of how cognitive processes correspond to patterns of brain activity. They may also allow to advance clinical applications of MRI, because in the clinical setting making diagnoses for single cases is essential.

Non-optimal task selection, such as too many, too little, too difficult, too easy series of tasks, incorrect type of tasks, suboptimal order, etc., may result in an incorrect diagnoses. Furthermore, it may result in an increase in MRI scanning time, which may create discomfort for the patient.

SUMMARY OF THE INVENTION

There may, therefore, be a need for improvement of the MRI workflow.

The object of the present invention is solved by the subject-matter of the appended independent claims, wherein further embodiments are incorporated in the dependent claims.

According to a first aspect of the present invention, there is provided a recommender system. The recommender system comprises an input unit, a processing unit, and an output unit. The input unit is configured to receive data comprising information about a plurality of pre-tests provided to a patient and associated pre-test results. The plurality of pre-tests is performed prior to an MRI scan session. The plurality of pre-tests comprises a cognitive test, a sensorimotor test, or a combination thereof. The processing unit is configured to generate, based on the received data, a cognitive profile of the patient indicative of an individual's pattern of relative strengths and difficulties across several cognitive domains. The processing unit is further configured to determine, based on the cognitive profile of the patient, a task implementation for the MRI scan session. The processing unit is further configured to provide, via the output unit, a recommendation of the determined task implementation for the MRI scan session.

The recommender system and method as described herein may allow to adapt and customize neurocognitive tests for use in MRI. This is done by using a pre-selection process before patients enter the scanner. The pre-selection includes a series of cognitive tests and/or other kind of pre-tests such as motor scanning or eye tracking. That is applying a systematic procedure for selecting tests for functional MR imaging and adapting them to the individual differences. The pre-test results will support the recommender system for improved selection of cognitive tasks and task parameters that will be presented during scanning. This may help to reduce scan time by adapting and tuning the tasks to the individual's profile of cognitive dysfunction, and increase test's results reliability. Additionally, the recommender system and method as described herein may also help patients to have a brief practice task to familiarize themselves with the tasks, resulting in a more efficient and time reducing clinical assessment/MRI scanning protocol.

According to an example of the present disclosure, the processing unit may be further configured to determine, based on the cognitive profile of the patient, whether a brain scan is necessary, and to provide, via the output unit, a recommendation of whether the patient needs a brain scan.

For example, the cognitive profile of the patient may be compared with that of a normative group to determine whether the patient has normal cognitive ability across several cognitive domains or deficits in certain cognitive domain, and then it is determined whether to perform a brain scan.

According to an example of the present disclosure, if it is determined that the patient needs a brain scan, the processing unit may be further configured to determine, based on the cognitive profile of the patient, at least one task for the patient to be performed in the MRI scan session, and to provide, via the output unit, a recommendation of the at least one task.

For example, the recommender system may detect brain abnormalities that could underlie the patient's specific profile of cognitive problems, and determine a task during MRI scanning to push the performance requirements to the limits of available cognitive resources such that the specific cognitive impairment can become visible.

According to an example of the present disclosure, the processing unit may be further configured to determine, based on the cognitive profile of the patient, a type and a task parameter of the at least one task, and to provide, via the output unit, the type and the task parameter of the at least one task.

According to an example of the present disclosure, the type of the at least one task comprises a task or a combination of tasks measuring one or more cognitive and sensorimotor functions.

Examples of the one or more cognitive and sensorimotor functions may include, but are not limited to, attention, language, memory, executive function, etc.

According to an example of the present disclosure, the task parameter may comprise a difficulty level, a stimulus type, an intensity, a task duration, or any combination thereof.

According to an example of the present disclosure, the at least one determined task may comprise a series of tasks. The processing unit may be configured to determine, based on a pre-defined selection protocol, an order of the tasks to be performed in the MRI scan session, and to provide, via the output unit, a recommendation of the order of the tasks.

According to an example of the present disclosure, the processing unit may be configured to identify, based on the cognitive profile of the patient, a potential cognitive problem of the patient, to select a type of scan that is suitable to detect brain abnormalities that underlie the patient's potential cognitive problem, and to provide, via the output unit, a recommendation of the type of scan.

The type of scan may include functional MRI or structural MRI. For example, reduced processing speed would require investigation of connectivity problems e.g. through diffusion tensor imaging (DTI) of white matter, whereas episodic memory retrieval problems would require more focal investigation of the medial temporal lobe e.g. using fMRI scanning. In this way, an appropriate type of scan is selected to better fit the cognitive profile of the individual patient.

According to an example of the present disclosure, the processing unit may be configured to identify, based on the cognitive profile of the patient, a potential cognitive problem of the patient, to determine, based on the determined potential cognitive problem of the patient, a brain area most likely to be affected, and to provide, via the output unit, a recommendation of the brain area to be scanned.

In this way, the scanning may be targeted to specific areas and does no longer necessarily involve the entire brain.

According to an example of the present disclosure, the input unit may be further configured to receive MRI data acquired in the MRI scan session using the at least one recommended task. The processing unit may be configured to determine, based on the MRI data, at least one modified task for a next MRI scan session, and to provide, via the output unit, a recommendation of the at least one modified task for the next MRI scan session.

This may enable a closed loop of continuous and supervised learning, enabling a strategy to continually improve a machine learning model for determining which task and which task parameters (e.g. difficulty level, stimulus type, stimulus intensity, task duration, or any combination thereof) can better fit the cognitive profile of the individual patient.

According to an example of the present disclosure, the processing unit may be configured to apply a trained machine-learning model to determine the task implementation.

According to a second aspect of the present invention, there is provided a magnetic resonance imaging (MRI) system. The MRI system comprises a recommender system according to the first aspect and any associated example for providing a recommendation of a task implementation in the MRI scan session, and an MRI scanner configured to acquire image data of a patient based on the recommendation provided by the recommender system.

The MRI scanner may be used as a functional MRI scanner or a structural MRI scanner.

According to a third aspect of the present invention, there is provided a method for determining MRI scanning tasks. The method comprises the steps of:

- receiving data comprising information about a plurality of pre-tests provided to the patient and associated pre-test results, wherein the plurality of pre-tests is performed prior to an MRI scan session, and wherein the plurality of pre-tests comprises a cognitive test, a sensorimotor test, or a combination thereof;
- generating, based on the received data, a cognitive profile of the patient, wherein the cognitive profile indicates an individual's pattern of relative strengths and difficulties across several cognitive domains;
- determining, based on the cognitive profile of the patient, a task implementation in the MRI scan session; and
- providing a recommendation of the determined task implementation.

The method may be at least partly computer-implemented, and may be implemented in software or in hardware, or in software and hardware. Further, the method may be carried out by computer program instructions running on means that provide data processing functions. The data processing means may be a suitable computing means, such as an electronic control module etc., which may also be a distributed computer system. The data processing means or the computer, respectively, may comprise of one or more processors, a memory, a data interface, or the like.

According to another aspect of the present invention, there is provided a computer program product comprising instructions which, when the program is executed by one or more processing units, cause the one or more processing units to carry out the steps of the method according to the third aspect and any associated example.

According to another aspect of the present invention, there is provided a computer-readable data carrier having stored thereon the computer program product.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

MRI, such as fMRI, is used to determine the spatial layout of brain activation associated with specific cognitive tasks. The main shortcoming of the current approach may be that scanner-tasks are not customized. In other words, at the present clinical neuropsychological assessments are done using standardized tasks (e.g. cognitive tasks) or series of tasks during scanning. Consequently, MRI data obtained may provide incorrect information and therefore erroneous diagnosis.

Figure 1:
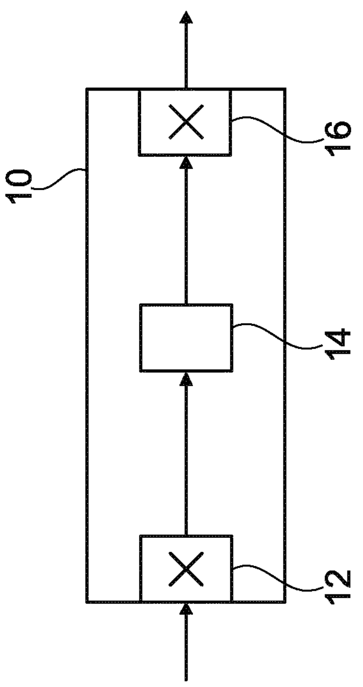
FIG. 1 illustrates a block diagram of an exemplary recommender system.

Towards this end, a recommender system is provided to use cognitive pre-testing to select MRI scanning tasks. An exemplary recommender system 10 is shown in FIG. 1. The exemplary recommender system 10 comprises an input unit 12, one or more processing units 14, and an output unit 16.

In general, the recommender system 10 may comprise various physical and/or logical components for communicating and manipulating information, which may be implemented as hardware components (e.g., computing devices, processors, logic devices), executable computer program instructions (e.g., firmware, software) to be executed by various hardware components, or any combination thereof, as desired for a given set of design parameters or performance constraints. Although FIG. 1 may show a limited number of components by way of example, it can be appreciated that a greater or a fewer number of components may be employed for a given implementation.

In some implementations, the recommender system 10 may be embodied as, or in, a device or recommender system, such as a server, workstation, or mobile device. The recommender system 10 may comprise one or more microprocessors or computer processors, which execute appropriate software. The processing unit 14 of the recommender system 10 may be embodied by one or more of these processors. The software may have been downloaded and/or stored in a corresponding memory, e.g., a volatile memory such as RAM or a non-volatile memory such as flash. The software may comprise instructions configuring the one or more processors to perform the functions as described herein.

It is noted that the recommender system 10 may be implemented with or without employing a processor, and also may be implemented as a combination of dedicated hardware to perform some functions and a processor (e.g., one or more programmed microprocessors and associated circuitry) to perform other functions. For example, the functional units of the recommender system 10, e.g., the input unit 12, the one or more processing units 14, and the output unit 16 may be implemented in the device or recommender system in the form of programmable logic, e.g., as a Field-Programmable Gate Array (FPGA). In general, each functional unit of the recommender system may be implemented in the form of a circuit.

In some implementations, the recommender system 10 may also be implemented in a distributed manner. For example, some or all units of the recommender system 10 may be arranged as separate modules in a distributed architecture and connected in a suitable communication network, such as a 3rd Generation Partnership Project (3GPP) network, a Long Term Evolution (LTE) network, Internet, LAN (Local Area Network), Wireless LAN (Local Area Network), WAN (Wide Area Network), and the like. For example, the recommender system may be implemented in a cloud-computing environment, which is a paradigm that moves resources, services and applications into a cloud enabling users to access and utilize the resources, services and applications.

The input unit 12 is configured to receive data comprising information about a plurality of pre-tests provided to a patient and associated pre-test results. The plurality of pre-tests is performed prior to an MRI scan session, e.g. before patient enters the scanner.

The plurality of pre-tests comprises a cognitive test, a sensorimotor test, or a combination thereof. Psychological testing may help inform the evaluation of an individual's functional capacity, particularly within the domain of cognitive functioning. The term "cognitive functioning" may encompass a variety of skills and abilities, including intellectual capacity, attention and concentration, processing speed, language and communication, visual-spatial abilities, and memory. Sensorimotor and psychomotor functioning may be measured alongside neurocognitive functioning in order to clarify the brain basis of certain cognitive impairments, and are therefore considered as one of the domains that may be included within a neuropsychological or neurocognitive evaluation. These skills and abilities may be evaluated in with formal standardized psychometric assessment. A typical psychological or neuropsychological evaluation is multifaceted and may include cognitive and non-cognitive assessment tools. Evaluations may comprise a clinical interview, administration of standardized cognitive or non-cognitive psychological tests, and professional time for interpretation and integration of data. The neuropsychological tests may be computer administered, or simply paper-and-pencil tests. The pre-tests may be administered either solely at home or in a sequence/combination of home, community-center, and specialized laboratory measurements.

The pre-test results of the patient may be stored in a database. The input unit 12 may retrieve the data from the database and provide the data to the processing unit 14.

The processing unit 14 is configured to generate, based on the received data, a cognitive profile of the patient indicative of an individual's pattern of relative strengths and difficulties across several cognitive domains. For example, the cognitive profile of the patient may indicate relative strengths and difficulties across the following six exemplary cognitive domains: general cognitive/intellectual ability, language and communication, memory acquisition, attention and distractibility, processing speed, and executive functioning. Each of these functional domains may be relevant for detecting brain abnormalities that underlie the patients' specific profile of cognitive problems.

The domain of general cognitive/intellectual ability may encompass reasoning, problem solving, and meeting cognitive demands of varying complexity. Tests of cognitive/intellectual functioning, commonly referred to as intelligence tests, may be used to evaluate the patient's pattern of relative strengths and difficulties in the domain of general cognitive/intellectual ability.

The domain of language and communication focuses on receptive and expressive language abilities, including the ability to understand spoken or written language, and communicate thoughts. Tests, such as Boston Naming Test, and the Boston Diagnostic Aphasia Examination, may be used to evaluate the patient's pattern of relative strengths and difficulties in the domain of language and communication.

The domain of learning and memory focuses on the ability to register and store new information. Examples of tests for learning and memory deficits may include the Wechsler Memory Scale, Wide Range Assessment of Memory and Learning, etc., which may be used to assess the patient's pattern of relative strengths and difficulties in the domain of learning and memory.

The domain of attention and vigilance may encompass the ability to sustain focus of attention in an environment with ordinary distractions. Tests like the WAIS-IV working memory index, Digit Vigilance, etc., may be used to evaluate the patient's pattern of relative strengths and difficulties in the domain of learning and memory.

The domain of processing speed may reflect mental efficiency and is central to many cognitive functions. Tests for deficits in processing speed may include e.g. the WAIS-IV processing speed index and can be used to evaluate the patient's pattern of relative strengths and difficulties in the domain of processing speed.

The domain of executive functioning may include complex cognitive processes such as planning, prioritizing, organizing, decision making, etc. Tests like the Trail Making Test Part B and the Wisconsin Card Sorting Test may be used to evaluate the patient's pattern of relative strengths and difficulties in the domain of executive functioning.

The generated cognitive profile of the patient may comprise the above-mentioned exemplary cognitive domains and/or other suitable cognitive domains.

Based on the generated cognitive profile of the patient, the processing unit 14 is configured to determine a task implementation of the MRI scan session.

In some examples, the processing unit 14 may be configured to determine, based on the cognitive profile of the patient, whether a brain scan is necessary, and provide, via the output unit, a recommendation of whether the patient needs a brain scan. For example, the processing unit 14 may compare the generated cognitive profile of the patient with a known cognitive profile of a normative group, i.e. a group of individuals that has normal or typical cognitive profile in response to that being tested. If the performances across all cognitive domains in the generated cognitive profile fall within a predefined acceptable range, the processing unit 14 may determine that a brain scan is not necessary.

In some examples, if it is determined that the patient needs a brain scan, the processing unit 14 may be further configured to determine, based on the cognitive profile of the patient, at least one task for the patient to be performed in the MRI scan session, and provide, via the output unit, a recommendation of the at least one task. The at least one task comprises a cognitive task, a sensorimotor task, or a combination thereof. The at least one task may be selected from a multitude of predetermined tasks by a recommender system based on the results of the cognitive pre-tests, this could involve an automatic analysis of e.g. specific memory, language, vision, and/or attention task-results leading to automatic action of the recommender system. Not only the type of task, but also the specific task parameters may be determined within the pre-screening unit. The type of the at least one task may comprise a task or a combination of tasks measuring one or more cognitive and sensorimotor functions including, but not limited to, attention, language, memory, and executive functions. Examples of the task parameter may comprise a difficulty level, a stimulus type, an intensity, a task duration, or any combination thereof. For example, a particular patient complains about memory problems. Careful administration of an elaborate neuropsychological test battery may reveal underlying problems with sustained attention rather than memory problems per se. The impairment does not become visible unless performance requirements are pushed to the limits of available cognitive resources. Therefore, the processing unit 14 may recommend presenting a vigilance task during fMRI scanning rather than a memory task. Performance requirements may be stretched by elongating task duration, degrading task stimuli and extending of interstimulus intervals, as this will likely provide the right circumstances to evoke the subtle impairment in sustained attention.

In some examples, the at least one determined task may comprise a series of tasks. The processing unit may be configured to determine, based on a pre-defined selection protocol, an order of the tasks to be performed in the MRI scan session, and provide, via the output unit, a recommendation of the order of the tasks. The pre-defined selection protocol may be provided by a user via a user interface or derived from previous examinations.

In some examples, the processing unit 14 may be configured to identify, based on the cognitive profile of the patient, a potential cognitive problem of the patient. For example, the processing unit 14 may compare the generated cognitive profile of the patient with that of a normative group. If the performances of the patient fall within the mildly to moderately impaired range in a cognitive domain, an interpretation of some degree of specific cognitive deficits in that cognitive domain may be appropriate. Then the processing unit 14 may be configured to select a type of scan that is suitable to detect brain abnormalities that underlie the patient's potential cognitive problem, and provide, via the output unit, a recommendation of the type of scan. The type of scan may include structural MRI and functional MRI. In other words, the information gathered during pre-tests is used to select the type of scan most suitable to detect brain abnormalities that underlie the patients' specific profile of cognitive problems. For example, reduced processing speed would require investigation of connectivity problems e.g. through DTI scanning of white matter, whereas episodic memory retrieval problems would require more focal investigation of the medial temporal lobe e.g. using fMRI scanning.

In some examples, the processing unit 14 may be configured to identify, based on the cognitive profile of the patient, a potential cognitive problem of the patient. For example, the processing unit 14 may compare the generated cognitive profile of the patient with that of a normative group. If the performances of the patient fall within the mildly to moderately impaired range in a cognitive domain, an interpretation of some degree of specific cognitive deficits in that cognitive domain may be appropriate. Then, the processing unit 14 may be configured to determine, based on the determined potential cognitive problem of the patient, a brain area most likely to be affected, and provide, via the output unit, a recommendation of the brain area to be scanned. In other words, the brain area most likely to be affected based on the individual's cognitive profile may be determined. In some examples, the processing unit 14 may be configured to map the cognitive test results to neuronal networks that need be evaluated with the scanning tasks. The scanning can be targeted to specific areas and does no longer necessarily involve the entire brain. As an example, different cognitive mechanisms may underlie an attention problem. As a pre-scanning cognitive test, an attentional network task may be administered to dissociate alerting, orienting and executive control. This may provide insight into which mechanism is primarily disturbed in a particular patient and what brain area is most likely to be involved. For example, alerting co-occurs with activation of the thalamus, anterior and posterior cortical sites, orienting is linked to activation of parietal sites and frontal eye fields, whereas the executive control is linked to activation of the anterior cingulate and other areas. Subsequently, fMRI scan protocol may be adapted accordingly.

In some examples, the input unit 12 may be further configured to receive MRI data acquired in the MRI scan session using the at least one recommended task. The processing unit 14 may be configured to determine, based on the MRI data, at least one modified task for a next MRI scan session, and to provide, via the output unit, a recommendation of the at least one modified task for the next MRI scan session. For example, a machine learning model may be implemented to provide the recommendation. It is possible to rate the recommended task based on the image data acquired in the MRI scan session using the recommended task. This may enable a closed loop of continuous and supervised learning, enabling a strategy to continually improve the machine learning model for determining which task and which task parameters (e.g. difficulty level, stimulus type, stimulus intensity, task duration, or any combination thereof) can better fit the cognitive profile of the individual patient. In addition, the closed training loop may enable the creation of models trained on very large amounts of data without compromising data privacy.

As an example, the processing unit 14 may include an artificial intelligence (AI) module using a pre-trained AI model for relating the generated cognitive profile to one or more tasks to be implemented in the MRI scanning session. The AI model may be pre-trained using the known ground truth samples that can be obtained from previous examinations. Examples of the AI models may include, but are not limited to, support vector machine (SVM), convolutional neural network (CNN), etc. The AI module may be continuously improved using the above-described closed loop of continuous and supervised learning with the aid of image data acquired from the patient who performed the recommended tasks. In some examples, a medical doctor may review/check the recommended task(s) and provide feedback, e.g. confirm/alter specific type of task and/or task parameter(s). Putting this expert feedback into the continuous learning loop implements an even more reliable strongly-supervised learning strategy.

The output unit 16 is configured to provide a recommendation of the determined task implementation for the MRI scan session.

In some examples, the recommendation may be displayed. If it is determined that a brain scan is not necessary, information like "brain scan not recommended" may be displayed. If it is determined that a brain scan is required, one or more of the following information may be provided and displayed: brain area to be scanned, type of scan (e.g. functional MRI or structural MRI), type of the task(s) (e.g. tasks for evaluating intellectual capacity, attention and concentration, processing speed, language and communication, visual-spatial abilities, memory, or any combination thereof), one or more task parameters of the task(s) (e.g. difficulty level, stimulus type, stimulus intensity, task duration, or any combination thereof), and order of the tasks if two or more task are recommended. The patient can perform the recommended task(s) in the MRI scan session.

In some examples, the recommendation may be stored e.g. in an in-house storing system or a web-based storing system.

The recommender system and method as described herein may allow to adapt neurocognitive tests for use in MRI scan on individual level. Providing a cognitive pre-testing on patients on individual level may help to improve clinical neuropsychological protocol, assessment and diagnosis.

Figure 2:
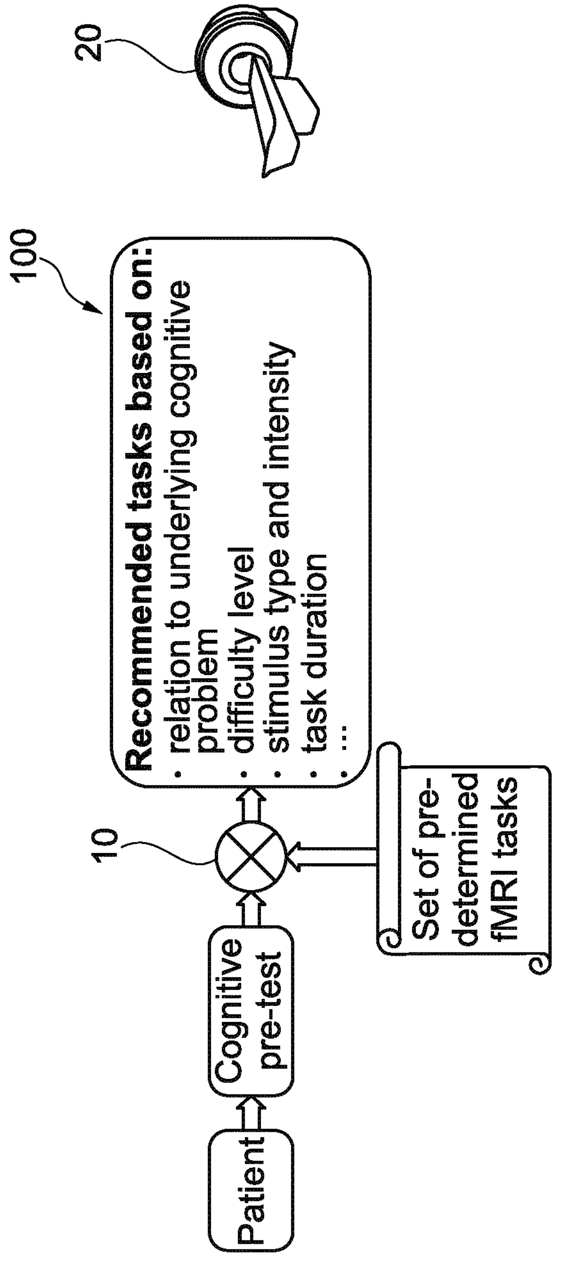
FIG. 2 illustrates an exemplary MRI system.

FIG. 2 schematically illustrates an MRI system 100. The MRI system 100 comprises a recommender system 10 and an MRI scanner 20.

As described above, the recommender system 10 receives data comprising information about a plurality of pre-tests provided to a patient and associated pre-test results. The plurality of pre-tests is performed prior to an MRI scan session. The pre-tests may comprise cognitive tests, which may be computer administered, or simply paper-and-pencil tests. The pre-tests may be administered either solely at home or in a sequence/combination of home, community-center, and specialized laboratory measurements. Other pre-tests, such as sensorimotor and psychomotor functioning, may be measured alongside neurocognitive functioning in order to clarify the brain basis of certain cognitive impairments. The information about the plurality of pre-tests provided to a patient and associated pre-test results may be provided by a user via a user interface or may be retrieved from a database that stores the pre-test results.

Based on the pre-test results, the recommender system 10 is configured to provide a recommendation of task implementation for the MRI scan session according to the method as described herein. The recommendation of task implementation may include whether to perform a brain scan. If a brain scan is recommended, the recommendation of task implementation may further include one or more of the following parameters: brain area to be scanned, type of scan (e.g. functional MRI or structural MRI), type of the task(s) (e.g. tasks for evaluating intellectual capacity, attention and concentration, processing speed, language and communication, visual-spatial abilities, memory, or any combination thereof), one or more task parameters of the task(s) (e.g. difficulty level, stimulus type, stimulus intensity, task duration, or any combination thereof), and order of the tasks if two or more task are recommended. In the example shown in FIG. 2, the recommender system 10 may select one or more tasks from a set of predetermined fMRI tasks. The patient can perform the recommended task(s) in the MRI scan session.

Figure 3:
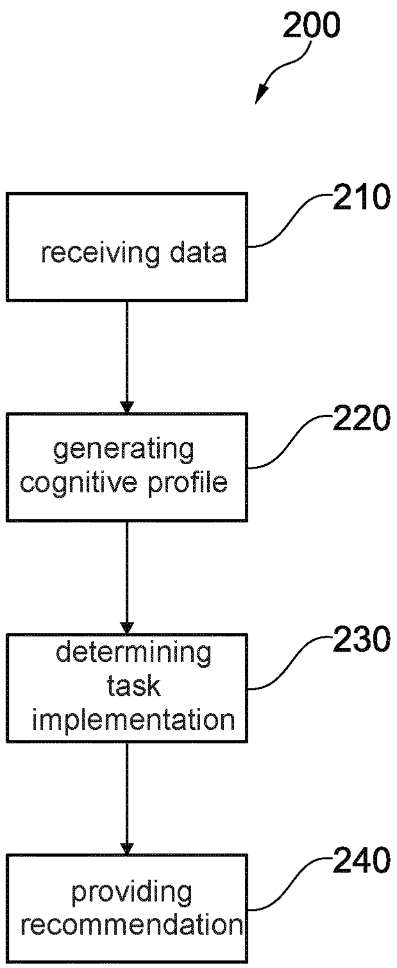
FIG. 3 illustrates a flow chart of an exemplary method.

FIG. 3 illustrates a flow chart describing an exemplary method 200 according to an embodiment of the present disclosure.

The method 200 may be implemented as a device, module or related component in a set of logic instructions stored in a non-transitory machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof. For example, computer program code to carry out operations shown in the method 200 may be written in any combination of one or more programming languages, including an object oriented programming language such as JAVA, SMALLTALK, C++, Python, or the like and conventional procedural programming languages, such as the "C" programming language or similar programming languages. For example, the exemplary method may be implemented as the recommender system 10 shown in FIG. 1 or FIG. 2.

At block 210, data is received, e.g. by the recommender system 10 shown in FIGS. 1 and 2. The received data comprises information about a plurality of pre-tests provided to the patient and associated pre-test results. The plurality of pre-tests is performed prior to an MRI scan session.

The plurality of pre-tests comprises a cognitive test, a sensorimotor test, or a combination thereof. The cognitive test may encompass a variety of tests for evaluating skills and abilities including intellectual capacity, attention and concentration, processing speed, language and communication, visual-spatial abilities, and memory. Sensorimotor and psychomotor functioning may be measured alongside neurocognitive functioning in order to clarify the brain basis of certain cognitive impairments, and are therefore considered as one of the domains that may be included within a neuropsychological or neurocognitive evaluation.

At block 220, based on the received data, a cognitive profile of the patient is generated. The cognitive profile indicates an individual's pattern of relative strengths and difficulties across several cognitive domains, such as domains of general cognitive/intellectual ability, language and communication, memory acquisition, attention and distractibility, processing speed, and executive functioning.

At block 230, based on the cognitive profile of the patient, a task implementation in the MRI scan session is determined. This will be explained in detail hereinafter and in particular with respect to the example shown in FIG. 4.

At block 240, a recommendation of the determined task implementation is provided. The patient may perform the recommended task(s) in the MRI scanning session. In some examples, a medical doctor may check the recommended task(s) and revise the recommended task(s), and the patient may perform the revised recommended task(s) in the MRI scanning session.

Figure 4:
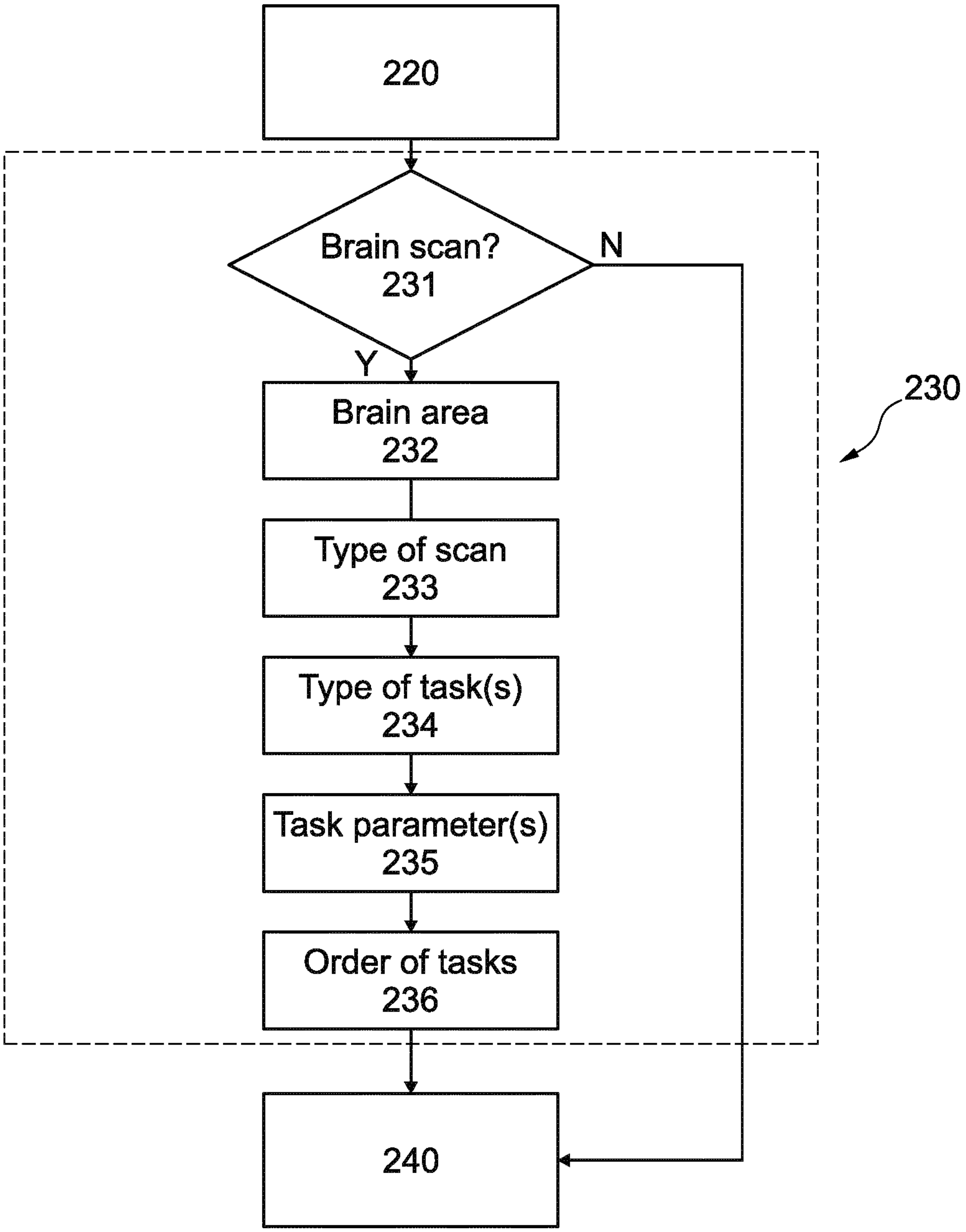
FIG. 4 illustrates a flow chart describing exemplary steps performed at block 230 of FIG. 3.

FIG. 4 illustrates a flow chart describing exemplary steps to be performed at block 230 of FIG. 3.

After the generation of cognitive profile of the patient at block 220, it is determined, based on the generated cognitive profile of the patient whether a brain scan is necessary. For example, the performance of the patient in the pre-tests may be compared with performance by a normative group to determine whether the patient has normal cognitive ability across all cognitive domains or the performances of the patient in certain cognitive domain fall within the mildly to severely impaired range. If the patient has normal cognitive ability across all cognitive domains, it is determined that a brain scan is not necessary and a recommendation will be provided at block 240. On the other hand, if the performances of the patient in certain cognitive domain fall within the mildly to severely impaired range, it may be determined at block 232, which brain area most likely to be affected based on the individual's cognitive profile. In this way, the scanning can be targeted to specific areas and does no longer necessarily involve the entire brain. As an example, the attentional network task may be administered to dissociate alerting, orienting and executive control. This will provide insight into which mechanism is primarily disturbed in a particular patient and what brain area is most likely to be involved. In some examples, as shown at block 232, a type of scan (e.g. functional MRI or structural MRI) may be determined. For example, reduced processing speed would require investigation of connectivity problems e.g. through DTI scanning of white matter, whereas episodic memory retrieval problems would require more focal investigation of the medial temporal lobe through fMRI scanning. In some examples, as shown at block 234, the task type may be determined based on the cognitive profile of the patient. For example, based on the results of the cognitive pre-tests, one or more of memory, language, vision, and/or attention tasks may be recommended to push the limits of available cognitive resources such that the particular cognitive impairment can become visible. In some examples, as shown at block 235, the task parameters, such as a difficulty level, a stimulus type, an intensity, a task duration, or any combination thereof, may also be determined based on the cognitive profile of the patient. In some examples, as shown at block 236, if two or more tasks are recommended, the order of the tasks may also be determined. The above-determined parameters may be provided as a recommendation of task implementation at block 240.

The above-described parameters may be determined in several ways. For example, the recommender system 10 shown in FIG. 1 or FIG. 2 may perform a search in a database that comprises information about previous examinations of a plurality of patients and select patient(s) with similar cognitive profile. The above-described parameters may be determined based on the tasks performed by the selected patient(s). In some example, a pre-trained AI model may be used to relate the generated cognitive profile to one or more tasks to be performed in the MRI scanning session. The AI model may be pre-trained using the known ground truth samples that can be obtained from previous examinations.

It should also be understood that, unless clearly indicated to the contrary, in any methods claimed herein that include more than one step or act, the order of the steps or acts of the method is not necessarily limited to the order in which the steps or acts of the method are recited.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A recommender system, comprising:

an input unit;

a processing unit; and an output unit;

wherein the input unit is configured to receive data comprising information about a plurality of pre-tests provided to a patient and associated pre-test results, wherein the plurality of pre-tests is performed prior to an MRI scan session, and wherein the plurality of pre-tests comprises a cognitive test, a sensorimotor test, or a combination thereof;

wherein the processing unit is configured to:

generate, based on the received data, a cognitive profile of the patient indicative of an individual's pattern of relative strengths and difficulties across several cognitive domains, determine, based on the cognitive profile of the patient, a task implementation for the MRI scan session, and provide, via the output unit, a recommendation of the determined task implementation for the MRI scan session.

2. The recommendation system according to claim 1, wherein the processing unit is further configured to determine, based on the cognitive profile of the patient, whether a brain scan is necessary, and to provide, via the output unit, a recommendation of whether the patient needs a brain scan.

3. The recommender system according to claim 2, wherein if it is determined that the patient needs a brain scan, the processing unit is further configured to determine, based on the cognitive profile of the patient, at least one task for the patient to be performed in the MRI scan session, and to provide, via the output unit, a recommendation of the at least one task.

4. The recommender system according to claim 3, wherein the processing unit is further configured to determine, based on the cognitive profile of the patient, a type and a task parameter of the at least one task, and to provide, via the output unit, the type and the task parameter of the at least one task.

5. The recommender system according to claim 4, wherein the type of the at least one task comprises a task or a combination of tasks measuring one or more cognitive and sensorimotor functions.

6. The recommender system according to claim 4, wherein the task parameter comprises a difficulty level, a stimulus type, an intensity, a task duration, or any combination thereof.

7. The recommender system according to claim 3, wherein the at least one determined task comprises a series of tasks; and wherein the processing unit is configured to determine, based on a pre-defined selection protocol, an order of the tasks to be performed in the MRI scan session, and provide, via the output unit, a recommendation of the order of the tasks.

8. The recommender system according to claim 3, wherein the processing unit is configured to identify, based on the cognitive profile of the patient, a potential cognitive problem of the patient, to select a type of scan that is suitable to detect brain abnormalities that underlie the patient's potential cognitive problem, and to provide, via the output unit, a recommendation of the type of scan.

9. The recommender system according to claim 3, wherein the processing unit is configured to identify, based on the cognitive profile of the patient, a potential cognitive problem of the patient, to determine, based on the determined potential cognitive problem of the patient, a brain area most likely to be affected, and to provide, via the output unit, a recommendation of the brain area to be scanned.

10. The recommender system according to claim 3, wherein the input unit is further configured to receive MRI data acquired in the MRI scan session using the at least one recommended task; and wherein the processing unit is configured to determine, based on the MRI data, at least one modified task for a next MRI scan session, and to provide, via the output unit, a recommendation of the at least one modified task for the next MRI scan session.

11. The recommender system according to claim 1, wherein the processing unit is configured to apply a trained machine-learning model to determine the task implementation.

12. A magnetic resonance imaging, MRI, imaging system, comprising:

a recommender system according to claim 1 for providing a recommendation of a task implementation in the MRI scan session; and an MRI scanner configured to acquire image data of a patient based on the recommendation provided by the recommender system.

13. A computer-implemented method, comprising:

receiving data comprising information about a plurality of pre-tests provided to the patient and associated pre-test results, wherein the plurality of pre-tests is performed prior to an MRI scan session, and wherein the plurality of pre-tests comprises a cognitive test, a sensorimotor test, or a combination thereof;

generating, based on the received data, a cognitive profile of the patient, wherein the cognitive profile indicates an individual's pattern of relative strengths and difficulties across several cognitive domains;

determining, based on the cognitive profile of the patient, a task implementation in the MRI scan session; and providing a recommendation of the determined task implementation.

14. A computer program product comprising instructions which, when the program is executed by one or more processing units, cause the one or more processing units to carry out the steps of the method of claim 13.

15. A non-transitory computer-readable medium having stored thereon the computer program product of claim 14.

* * * * *